United States Patent [19]

Brothers et al.

[11] Patent Number: 4,541,443

[45] Date of Patent: Sep. 17, 1985

[54] ABRADING/SMOOTHING TOOL

[76] Inventors: William S. Brothers, 1815 N. 1400 East; William H. Brothers, 101 W. 4800 North, both of Provo, Utah 84604

[21] Appl. No.: 492,808

[22] Filed: May 9, 1983

[51] Int. Cl.⁴ ............................................. A45D 29/04
[52] U.S. Cl. ................................... 132/75.6; 132/76.5
[58] Field of Search ..................... 132/75.6, 76.5, 73; 128/304, 355

[56] References Cited

U.S. PATENT DOCUMENTS

| | | | |
|---|---|---|---|
| 448,409 | 3/1891 | Cassidy | 132/75.6 |
| 1,067,280 | 7/1913 | Smilovetz | 132/76.5 |
| 1,513,838 | 11/1924 | McAuliffe | 132/76.5 |
| 1,588,160 | 6/1926 | Booty | 132/76.5 |

Primary Examiner—Gregory E. McNeill
Attorney, Agent, or Firm—B. Deon Criddle

[57] ABSTRACT

A tool for abrading or smoothing calluses or other areas of skin which includes one or more segments of abrasive screen supported by rigid arcuate or other shaped holder and an elongated handle of various shapes with the holder and abrasive screen mounted to the handle for easy manipulation by a user.

5 Claims, 8 Drawing Figures

U.S. Patent   Sep. 17, 1985   4,541,443
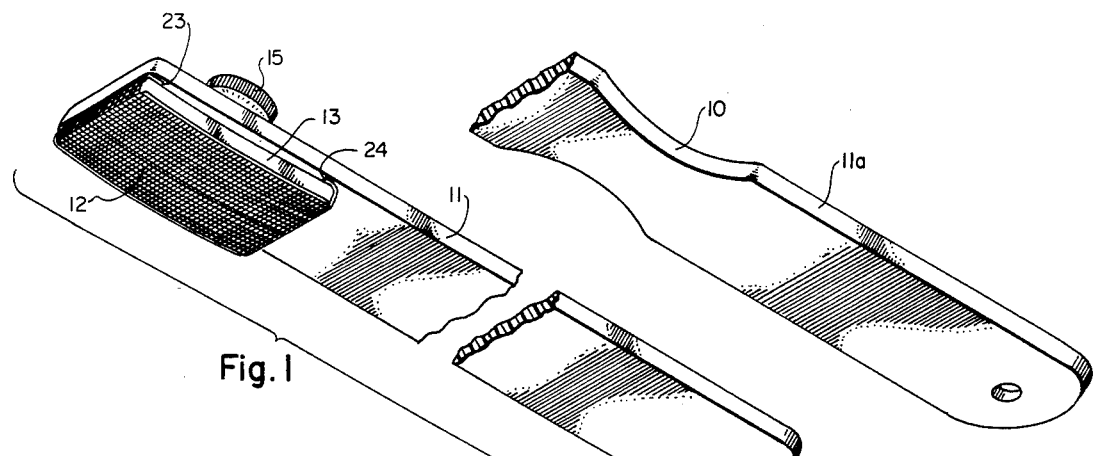
Fig. 1
Fig. 1a
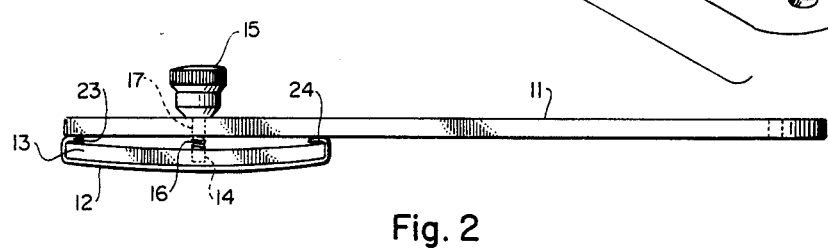
Fig. 2
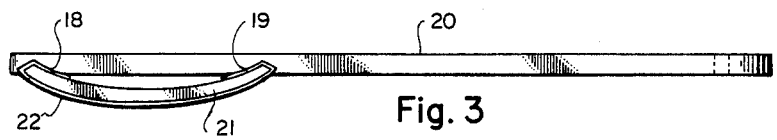
Fig. 3
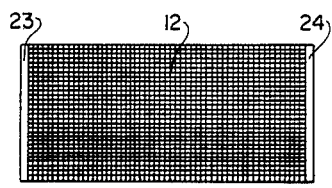
Fig. 4
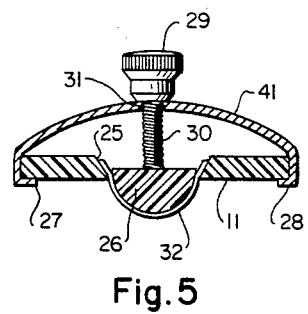
Fig. 5
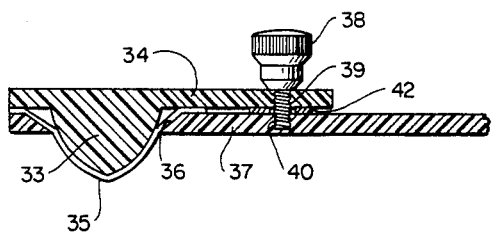
Fig. 6
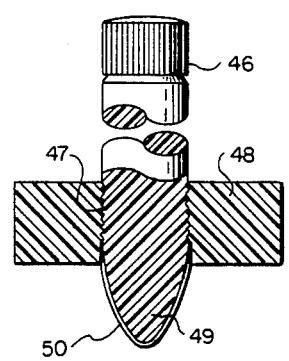
Fig. 7

4,541,443

ABRADING/SMOOTHING TOOL

BACKGROUND OF THE INVENTION

The present invention relates to a tool for abrading and/or smoothing skin.

For health, cosmetic and economic reasons it frequently becomes desirable or necessary to abrade or smooth skin. Health and cosmetic reasons include, among others, the reduction or smoothing of calluses, growths and irregular skin areas, the removal of dead skin and skin stimulation. Economic reasons include health cost savings and any economic value of cosmetic improvements, and may also include non-health expense reduction and convenience, for example benefits derived from smoothing of women's feet that become rough resulting in less snagged and ruined nylon stockings.

Such abrading or smoothing has usually involved action by an individual or by a professional acting upon an individual, scraping or paring the skin wlth a sharp knife or knife-like instrument or abrading the skin with sandpaper, emery cloth, pumice stone or a metal file. The use of any sharp instrument is tedious and dangerous, particularly for the unskilled or less than dextrous, as care must be exercised to avoid cutting too deep and causing injury to underlying tissue. Metal files are not generally acceptable for such use. not being designed for such use, being cumbersome and often being unpleasant to the touch, seeming cold.

The use of sandpaper or emery cloth has been effective, but not as effective as the proposed invention. Sandpaper or emery cloth material is usually wrapped around the ends of the user's fingers or around some other shaped item and then reciprocated or rotated over the area to be abraded or smoothed. Hand holding the material in place during use has been difficult and tiresome. Even if held by a device, sandpaper tends to crack and fray and the abrasive particles may separate from the backing material. Sandpaper and emery cloth must also be replaced frequently because of cracking and fraying and because the abrasive-surface voids become filled with abraded skin fragments. This may also result in an undesireable interruption of the abrading process.

Sandpaper and/or emery cloth has also been used on the vibrating or rotating surfaces of hand-held electrical appliances. Such devices are relatively heavy and cumbersome requiring close control and constant attention to avoid inlury to the area being abraded or smoothed or to surrounding tissue. Such devices are not well suited to most precision abrading or smoothing.

Pumice stone has been more commonly used for such abrading or smoothing. However, such pumice stone becomes smooth, losing abrasive quality with use as the voids in the abrasive surface become filled with abraded skin fragments. This requires perodic brushing or flushing with air or liquid to maintain the abrasive capability of the stone. Further pumice stones are fragile and often break with such use.

In addition, the prior known techniques do not lend themselves well to use by handicapped or older people whose manual dexterity is reduced or impaired.

SUMMARY AND OBJECTS OF THE INVENTION

An object of the present invention is to provide an abrading or smoothing tool for skin which is easy to handle and control, is comfortable to work with, and is useable at a variety of angles to accommodate abrading or smoothing of various body contours.

An additional object is to provide a tool which is durable and abrades or smoothes rapidly.

Another object is to provide an abrading and smoothing tool for skin which can be easily and quickly cleaned, washed or sanitized.

A turther object is to provide an easily assembled/-disassembled tool which has an easily replaceable abrasive surface.

The disadvantages of the prior known techniques are overcome in the present invention by provision of an abrading and smoothing tool which includes a handle adapted to be easily grasped by the user, a segment of abrasive screen secured to the exposed surface of a holder and means for removeably attaching the holder to the handle such that the abrasive screen can be reciprocated or rotated across an area of skin.

Other objects and features of the present invention will be apparent to those skilled in the art from the following detailed description taken in combination with the attached drawings.

BRIEF DESCRIPTION OF THE DRAWINGS

FIG. 1 is a perspective view of preferred embodiment of an abrading and smoothing tool according to the present invention;

FIG. 1a is a perspective view of an alternate handle configuration to FIG. 1;

FIG. 2 is an elevation view of the tool of FIG. 1;

FIG. 3 is an elevation view of another embodiment of said abrading and smoothing tool;

FIG. 4 is a plan view of an abrasive screen for use with tools of FIG. 1 and FIG. 3;

FIG. 5 is an elevation view partly in section of an attachment for use with the tools of FIG. 1 and FIG. 3;

FIG. 6 is an elevation view partly in section of another attachment configuration also showing a different configuration of abrading surface; and FIG. 7 is an elevation view partly in section of an additional attachment configuration also showing another different configuration of abrading surface.

DESCRIPTION OF THE PREFERRED EMBODIMENT

The abrading and smoothing tool of the present invention provides a means of holding an abrasive material in a fixed position on an exposed surface and a handle for easy manipulation of the abrasive against an area of skin. In addition, an abrasive screen material, which may include a small mesh metal screen impregnated with abrasive material, is provided as the abrading surface to facilitate ease of replacement and permit simple and rapid cleaning.

Referring to FIGS. 1, 1a and 2 of the drawing, the present tool is illustrated as including an elongated handle 11 of various lengths and of suitable flexible or rigid material, such as plastic, hard rubber, wood, metal, etc. Plastic, such as acrylic, etc., is preferred and may be clear or colored, but preferably is transparent so that a user can see through the handle to observe the skin area being abraded or smoothed. A segment of abrasive screen 12 such as silicone carbide sand screen is supported on the handle adjacent to one end thereof by means of a holder 13. The holder is formed of a short, generally rectangular section material, and is provided with an arcuate cross-section. The handle 11 may include indentation 10 or any form of notches, tapers, grooves, bends, curvature or other configuration change for holding the handle with the thumb and fingers or the palm of the hand for better ease in holding and/or for providing better control of the device or to accommodate particular uses and applications. The handle may also be other than rectangular in configuration and may also be of various lengths. The abrasive screen is positioned on the holder with the ends of the screen folded over the opposite extremities of the holder, which screen ends may be adhesive 23 and 24 as is discussed further below. An internally threaded bore 14 is provided in the approximate center of the concave surface of the holder. A knob 15 with an externally threaded shank 16 is positioned on the upper surface of the handle with the shank 16 extending through an opening 17. The distal end of the shank is received within bore 14 such that upon rotation of the knob the holder is drawn toward the handle, thus clamping the ends of the screen between the extremities of the holder and the lower surface of the handle. With this tool the abrasive screen is easy to remove and replace by loosening knob 15 until the ends of the screen are freed. A new screen is then positioned on the holder 13 and the ends folded over the extremities of the holder to extend between the holder and the handle. The knob is then tightened to clamp the ends of the screen and secure it firmly in place on the holder. The convex surface of the holder allows the abrasive screen to be maneuvered into hollows or depressions in the skin surface and allow abrading of a greater number of body angles and contours. The abrasive screen provides a very effective abrading surface which retains its abrasive characteristics and is easy to clean. What skin fragments may accumulate on the screen or in the openings of the screen may be easily removed by tapping and/or brushing. Cleaning may be easily accomplished by flushing with fluid and possible brushing or tapping. The tool can be easily dried by pressing or tapping against an absorbent material, such as a towel, and/or allowed to air dry. Such a configuration and the use of an abrading screen may be readily sterilized by washing in an appropriate cleaner, rinsing and soaking in a suitable antiseptic solution or material permitting heat sterilization.

An alternative construction is illustrated in FIG. 3 which includes a pair of grooves 18 and 19 machined or formed in the lower surface of the handle 20. The grooves are spaced apart and are oppositely directed at a slight angle, approximately 10–30 degrees from the horizontal. The degree of arc of the holder 21 is selected so that the opposite extremities coincide with the axes of the grooves. A segment 22 of abrasive screen is positioned on the convex surface of the holder and the ends folded over the extremities. The holder is positioned a the side of the handle with the extremities aligned with the grooves and then forced laterally into and upon the handle so that the extremities of the holder and the ends of the screen are received within the grooves. The holder is thus secured on the handle and the screen held in place on the holder. The dimensions of the grooves are selected to accommodate the combined thickness of the extremities and the screen with a snug fit to hold the abrasive screen in position during use. If desired, the holder could be formed of flexible material which could be inserted axially into the grooves by flexing the material instead of sliding laterally. The handle could also be formed of flexible material which could be slightly arched for the insertion of a flexible or rigid holder and then released to bind-fit the holder and screen in place.

As shown in FIG. 4 strips 23 and 24 of adhesive can be applied adjacent to each end of the segment 12 of abrasive screen. When the screen is positioned on the holder the ends of the screen adhere to the surface of the holder and maintain the screen in position on the convex surface during use. This feature is appropriate for users with impaired manual dexterity since the screen will not separate from the holder while the holder is being affixed to the handle.

The modifications illustrated in FIGS. 5, 6 and 7 are adaptable to the tool of either FIGS. 1 or 3. The handles 11 or 20 typically would have an enlarged opening near the end with flared edged as indicated at 25. A hemispherical holder 26 is provided with a diameter which is slightly larger than that of the smallest part of the opening 25. A metal clip 41 has the opposite ends bent inwardly to form ledges 27 and 28. A knob 29 with an elongated externally threaded shank 30 is threaded into an internally threaded opening 31 in the center of the clip with the shank extending into threads in or secured to holder 26. A segment of abrasive screen 32 is placed in the flared portion of the opening 25 with the holder above it. The clip is placed on the handle with the ledges 27 and 28 bearing against the lower surface of the handle. The knob 29 is then rotated to force the holder into the opening so that it protrudes below the lower surface of the handle. The center of the abrasive screen is thus forced through the opening by the spherical surface of holder 26 to form a rounded abrasive surface. This modification can be used for various abrading tasks, but is particularly useful for abrading small and curved areas.

A modified construction is illustrated in FIG. 6 in which a holder 34 with a pointed near-hemispherical lobe 33 is secured to handle 37. As in the embodiment of FIG. 5, a segment of abrasive screen 35 is placed in the flared portion of the opening 36 in the handle. The hemispherical holder 33 is positioned on the screen and in the opening. The holder is then clamped in place by means of a knob 38 having an externally threaded shank 39 which is received within a internally threaded bore 40 in the handle 37. Washer 42 is sized to provide a parallel fit of handle 37 and holder 34. the washer size being determined by the thickness of screen 35.

In the embodiment of FIG. 7 the opening in the handle 48 is enlarged and then internally threaded as at 47. A holder 49 of various possible lengths is externally threaded and is adapted to be received within the opening with a loose fit. A segment of abrasive screen 50 is fitted over the end of the holder, which is illustrated in FIG. 7 as being oblate, and the holder screwed into the opening by grapsing at 46 until the rounded end and the screen protrude beyond the lower surface of the handle 48. The relative dimensions of the external threads on the holder and the internal threads in the opening near the bottom of the opening should be such as to accommodate sufficient of the abrasive screen material to bind the screen in place upon tightening of the holder. Alternatively, the holder may removeably fit in the opening or be fixed and a small segment of abrasive screen may be attached to the holder surface by means of a suitable adhesive.

The tool of the present invention is particularly useful by persons whose movements and/or dexterity are impaired and who cannot effectively control prior art devices. The light weight, ease of manipulation and rapid abrading or smoothing of the present tool is a significant improvement over prior art. In addition, the present tool is anticipated to have wide application in connection with abrading and smoothing of calluses, particularly foot calluses.

It will be apparent to those skilled in the area that the aforementioned description is only an illustration of numerous methods which may be employed to practice the subject invention. With this in mind, it is to be understood that the scope of the invention is defined by the appended claims and is not to be limited by examples previously suggested.

What is claimed is:

1. An abrading and smoothing tool for reducing calluses and and the like, comprising
   an elongate handle made of transparent material;
   a holder, formed between opposite ends thereof and having a concave surface and a convex surface.
   a screen having an abrasive material surrounding the openings thereof on at least one face; and
   means for securing the holder to one end of the handle, with the screen pulled tightly over the convex surface and the ends thereof clamped and held between the opposite ends of the holder and the handle and having the surface thereof with abrasive material thereon turned outwardly with respect to said holder.

2. An abrading and smoothing tool as in claim 1, wherein the means for securing the holder to one end of the handle, comprises
   bolt means inserted through the handle near one end thereof and threaded into the concave surface of the holder.

3. An abrading and smoothing tool as in claim 2 wherein
   opposite ends of the screen are provided with adhesive means to bond the screen to opposite ends of the holder.

4. An abrading and smoothing tool as in claim 1, wherein the means for securing the holder to one end of the handle comprises
   a pair of grooves in the handle into which the ends of the holder and screen are inserted.

5. An abrading and smoothing tool as in claim 3, wherein the means for securing the holder to one end of the handle comprises
   a pair of grooves in the handle into which the ends of the holder and screen are inserted.

* * * * *